Figure 1A:
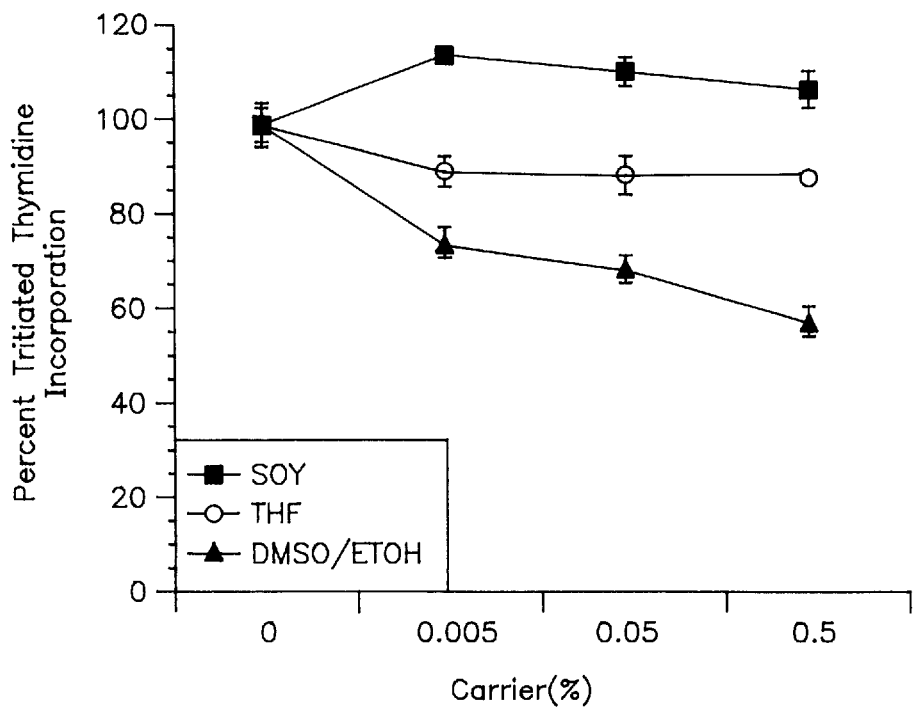

United States Patent [19]

Schlipalius

[11] Patent Number: 5,773,026

[45] Date of Patent: Jun. 30, 1998

[54] AQUEOUS FORMULATIONS OF WATER-INSOLUBLE THERAPEUTIC AGENT COMPRISING CAROTENOIDS AND/OR TOCOPHEROLS

[75] Inventor: Lance Elliott Schlipalius, Ashwood, Australia

[73] Assignee: Betatene Limited, Australia

[21] Appl. No.: 525,623

[22] PCT Filed: Mar. 22, 1994

[86] PCT No.: PCT/AU94/00143

§ 371 Date: Sep. 22, 1995

§ 102(e) Date: Sep. 22, 1995

[87] PCT Pub. No.: WO94/21232

PCT Pub. Date: Sep. 29, 1995

[30] Foreign Application Priority Data

Mar. 22, 1993 [AU] Australia .................. PL7935

[51] Int. Cl.⁶ .................................................. A61K 9/107
[52] U.S. Cl. ................. 424/450; 424/78.02; 424/531; 514/937
[58] Field of Search .................. 424/422, 450; 514/937

[56] References Cited

U.S. PATENT DOCUMENTS 4,572,915  2/1986  Crooks ........................... 514/458
4,680,314  7/1987  Nonomura ...................... 514/725

*Primary Examiner*—Raj Bawa
*Attorney, Agent, or Firm*—Burns, Doane, Swecker & Mathis, LLP

[57] ABSTRACT

The invention is a carotenoid agent for inhibiting the conversion of epithelial cells to tumours, the agent including an effective amount of a water insoluble carotenoid component in a suitable non-toxic carrier medium.

25 Claims, 5 Drawing Sheets

AQUEOUS FORMULATIONS OF WATER-INSOLUBLE THERAPEUTIC AGENT COMPRISING CAROTENOIDS AND/OR TOCOPHEROLS

FIELD OF THE INVENTION

The invention relates to a substantially non-toxic water dispersible therapeutic formulation including a substantially water insoluble therapeutic agent selected from the group consisting of carotenoid compositions and tocopherols that can be administered to animals, including humans, by injection or intravenously into the organs, blood stream or lymph.

BACKGROUND OF THE INVENTION

Some chemical compounds of physiological therapeutic significance have little or no water solubility. The water insolubility of these compositions limits the means by which those compounds can be administered to the body.

Included in the group of compounds that are considered to be of physiological importance are the carotenoids, tocopherols and other lipid based molecules used for various therapeutic purposes.

It has been hypothesised that carotenoids and in particular beta-carotene may reduce the risk of breast, lung, colon, prostate and cervical cancer, heart disease and stroke and may retard macular degeneration. In this respect, one hypothesis is that in mammals beta-carotene is converted to vitamin A and vitamin A analogues or retinoids (see Moon RC: Comparative aspects of carotenoids and retinoids as chemopreventive agents for cancer. J Nutr 119:127–134, 1989). It is this pro-vitamin A activity and the ability to prevent oxidative damage that has made carotenoids and in particular beta-carotene a compound of interest in chemopreventive studies. For instance, anti-oxidants are used, amongst other things, to quench free radicals that are by-products of normal metabolism in cells.

Beta-carotene has also been used in the treatment of erythropoietic protoporphyria (EPP). EPP is a genetic disease causing an inadequacy in the metabolism of porphyrin compounds. It results in a rapid blistering of the skin on exposure to sunlight.

When considering the use of these lipid based compositions for human application immediate difficulties arise because of their lipophyllic nature which renders them insoluble in water in useful quantities. It is believed that these products are transported in the bloodstream as low density lipoproteins.

The current principal means by which these therapeutic compositions are introduced into the body is orally. However, this method is often unsatisfactory because the poor absorption of these compositions by the alimentary canal limits the concentrations in the blood which can be achieved. Further, there will be a substantial delay before a required level of these compositions in the bloodstream or a specific organ is reached. Sometimes the required level cannot be reached as certain individuals do not absorb carotenoids, especially beta-carotene, very well. There is about a tenfold difference in the ability of human individuals to absorb beta-carotene. There have been over 500 carotenoids isolated, but only approximately 15 have been shown to occur in the bloodstream.

Physicians often seek to administer compounds by injection or by intravenous drip rather than oral ingestion. However, because of the virtual water insolubility of these therapeutic compositions it is very difficult to administer them either by injection or intravenously. Consequently, the compound must be made dispersible in an aqueous base so that it is available to the body's cells. In this regard, the base must be compatible with, for example, the bloodstream or lymph, and the material must be prepared in a biologically sterile form. The base must itself be non-toxic to the human cells.

To date several in vitro studies have taken place to determine the effect of beta-carotene on normal and transformed cell types using solvents to solubilise the beta-carotene such as tetrahydrofuran, butanol, chloroform, hexane, dimethylsulfoxide, ethanol or in a liposome micelle. Previous liposome preparations have shown toxicity in cell line cultures as well as being limited in application. (see Bertram J.S., Pung A, Churley M., et al: Diverse carotenoids protect against chemically induced neoplastic transformation. Carcinogenesis 12:671–678, 1991; Hazuka M.B., Prasad-Edwards J., Newman F., et al: Beta-carotene induces morphological differentiation and decreases adenylate cyclase activity in melanoma cells in culture. J Am Coll Nutr 9:143–149, 1990; Schultz T.D., Chew B.P., Seaman W.R., et al: Inhibitory effect of conjugated dienoic derivatives of linoleic acid and beta-carotene on the in vitro growth of human cancer cells. Canc Letters 63:125–133, 1992; Schwartz J.L., Shklar G.: The selective cytotoxic effect of carotenoids and a-tocopherol on human cancer cell lines in vitro. J Oral Maxillofac Surg 50:367-373, 1992; Schwartz J.L., Tanaka J., Khandekar V., et al: Beta-Carotene and/or Vitamin E as modulators of alkylating agents in SCC-25 human squamous carcinoma cells. Canc Chemother Pharmacol 29:207–213, 1992; Zhang L-X, Cooney R.V., Bertram J.S.: Carotenoids enhance gap junctional communication and inhibit lipid peroxidation in C3H/10T1/2 cells: relationship to their cancer chemopreventive action. Carcinogenesis 12:2109–2114, 1991; and Zhang L-X, Cooney R.V., Bertram J.S.: Carotenoids up-regulate connexin 43 gene expression independent of their provitamin A or anti-oxidant properties. Canc Res 52:5707–5712, 1992). However, these solvents have been found to have a toxic effect which is dose dependent. These solvents are also incompatible with human blood or lymph for the purposes of intravenous or injectable preparations.

Accordingly, investigations were carried out to develop a substantially non-toxic water dispersible therapeutic formulation including a substantially water insoluble therapeutic agent that can be administered to animals, including humans, by injection or intravenously into the organs, blood stream or lymph.

SUMMARY OF THE INVENTION

The invention generally provides a therapeutic formulation for administration by injection or intravenously, including a mixture of:

(a) a water soluble or dispersible component;

(b) an emulsifier component; and (c) a water insoluble therapeutic agent in a suitable carrier medium, wherein the water insoluble therapeutic agent is selected from the group consisting of carotenoid compositions and tocopherols.

In a preferred form of the invention, the water soluble or dispersible component is selected from sugar alcohols, sugars, amino acids, water, vitamins, blood serum or plasma, lymph, buffers and combinations and polymers of these materials, and injectables that are well known in the industry such as mineral salt preparations and dextrose solutions or combinations of these components.

Even more preferably, the water soluble or dispersible component is in the range of 30% to 90% by weight. More preferably the sugar alcohol is glycerol and in yet a further preferred embodiment, glycerol is in the range of 30% to 90% by weight.

In yet a further preferred embodiment of the invention, the emulsifier component is selected from glycerides (including preferably mono and diglyceride structures from plant and animal sources), polyglycerol esters, lecithins and other phospholipids. More preferably the glyceride is glyceryl mono-oleate. In yet a further preferred form of the invention, the emulsifier is in the range of 0.2% to 20% by weight and more preferably 1.0% to 10% by weight.

In another preferred form of the invention, the tocopherol is Vitamin E (D alpha tocopherol).

In yet a further preferred form of the invention, the carotenoid composition includes beta-carotene. In yet a further preferred form the water insoluble carotenoid composition includes 2% to 50% by weight beta-carotene in soya bean oil. More preferably, the carotenoid composition includes 20% to 40% and most preferably 30% by weight of beta-carotene in soya bean oil.

Preferably, the beta-carotene is a mixture of cis betacarotene and all trans beta-carotene. Typically, the cis betacarotene content of the beta-carotene is in the range of 50% and 90%, more preferably 70% and 85%. More preferably, the beta-carotene is predominantly 9 cis beta-carotene in a preferred range of 60% to 90%. In an even more preferred embodiment, the water insoluble therapeutic agent is in the range of 0.1% to 10% by weight (and more preferably 1% to 5% by weight) of the therapeutic formulation.

In yet a further preferred form of the invention, the carrier medium used to carry the water insoluble therapeutic agent selected from the group comprising fatty acids and triglyceride lipids and non-saponifiable lipid preparations, certain suitable petroleum hydrocarbons including octadecane and combinations of the foregoing compounds.

In yet a further preferred form of the invention, the triglyceride lipids are selected from the group comprising fats and/or oils derived from plant sources such as seed oils including soya bean, cotton seed and sunflower and from animal sources including fish and beef. More preferably, the carrier medium is in the range of 0.1% to 40% by weight and even more preferably 1% to 20%.

In an even more preferred form of the invention, the concentration level of the therapeutic formulation is diluted with the diluting solution selected from aqueous buffers, normal intravenous preparations (including isotonic saline or 5% dextrose solution) and blood serum and combinations of the foregoing for administration to cells in vivo and cell line culture media for administration to cells in vitro.

The term "mixture" as used herein is intended to include various physical forms including emulsions, solutions and crystal suspensions.

EXAMPLES

The following examples demonstrate the preparation and utilisation of the invention, that is, the preparation and use of a substantially non-toxic water dispersible therapeutic formulation including a substantially water insoluble therapeutic agent that can be administered to animals, including humans, by injection or intravenously into the organs, blood stream or lymph.

In particular, the following examples are directed to the formation of a beta-carotene containing composition and demonstrate the non-toxicity and solubility of that mixture on melanomas and melanocytes.

Figure 1B:
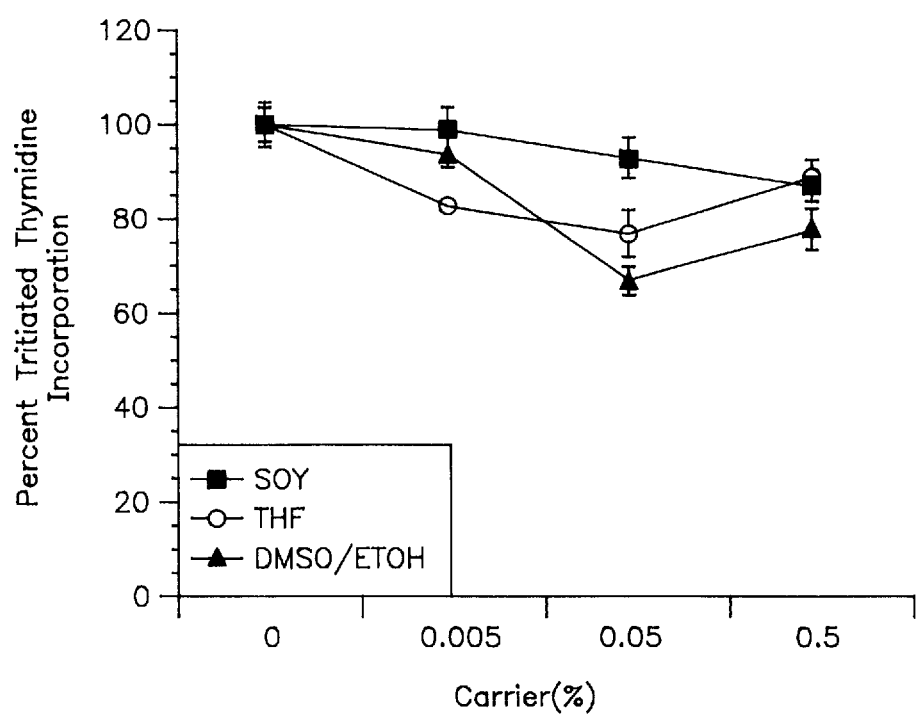

FIG. 1 are graphs showing the effect of carriers on DNA synthesis in human metastatic melanoma and neonatal melanocytes. In summary, the melanoma cell strain, c81-46a and melanocytes were incubated for 72 hours with soybean oil extract, tetrahydrofuran and a 3:1 mixture of dimethylsulfoxide:ethanol. Each data point is the mean of 6 wells ± percent standard error as compared to control.

Figure 2:
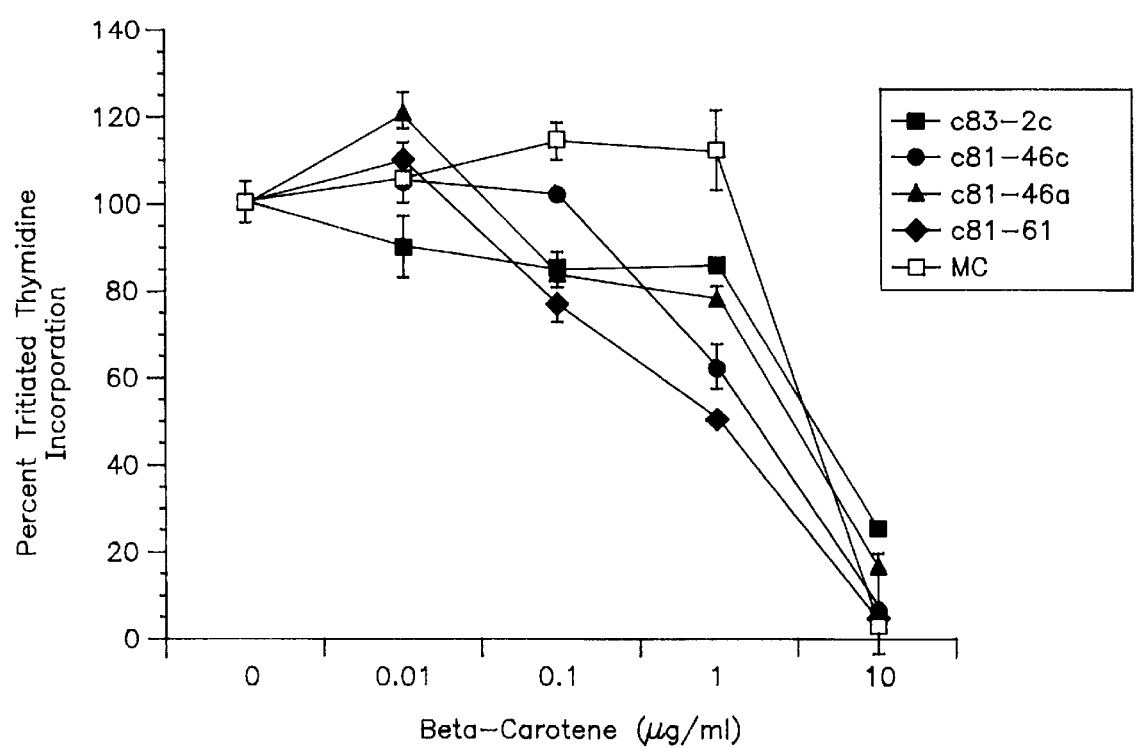

FIG. 2 is a graph showing the effect of beta-carotene on DNA synthesis in human metastatic melanoma and neonatal melanocytes. In summary, melanoma cell strains: c83-2c, c81-46c, c81-46a, c81-61 and melanocytes (MC) were incubated for 72 hours with beta-carotene. Each data point is the mean of 6 wells ± percent standard error as compared to control. Diluent (soy) concentration=0.05%.

Figure 3:
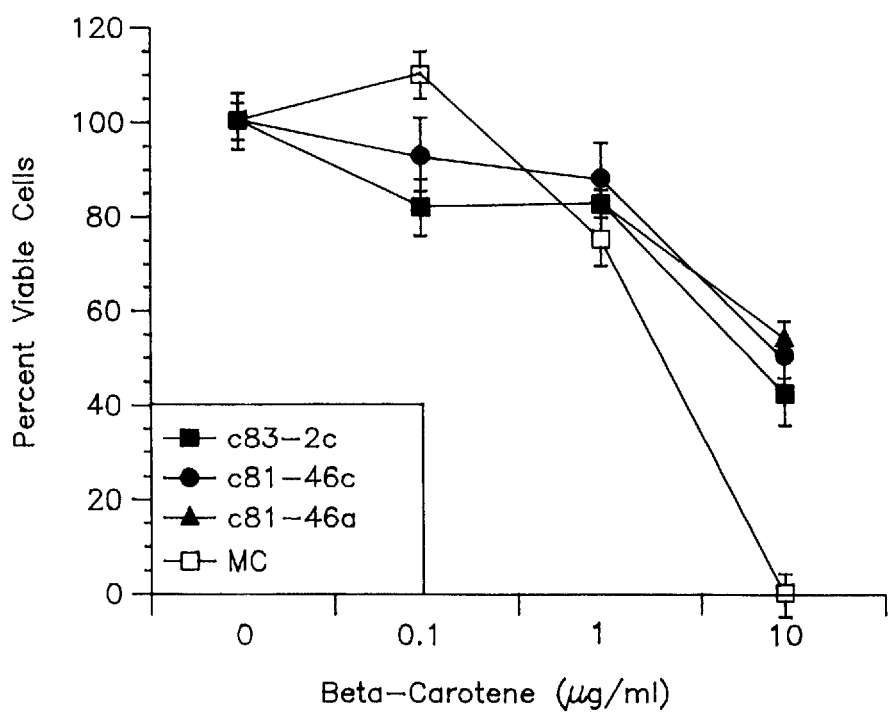

FIG. 3 is a graph showing the effect of beta-carotene on the proliferation of human metastatic melanoma and neonatal melanocytes. In summary, melanoma cell strains: c83-2c, c81-46c, c81-46a and melanocytes (MC) were incubated for 72 hours with beta-carotene and viability assessed by trypan blue exclusion. Each data point is the mean of 3 wells ± percent standard error as compared to control. Diluent (soy) concentration=0.05%.

Figure 4:
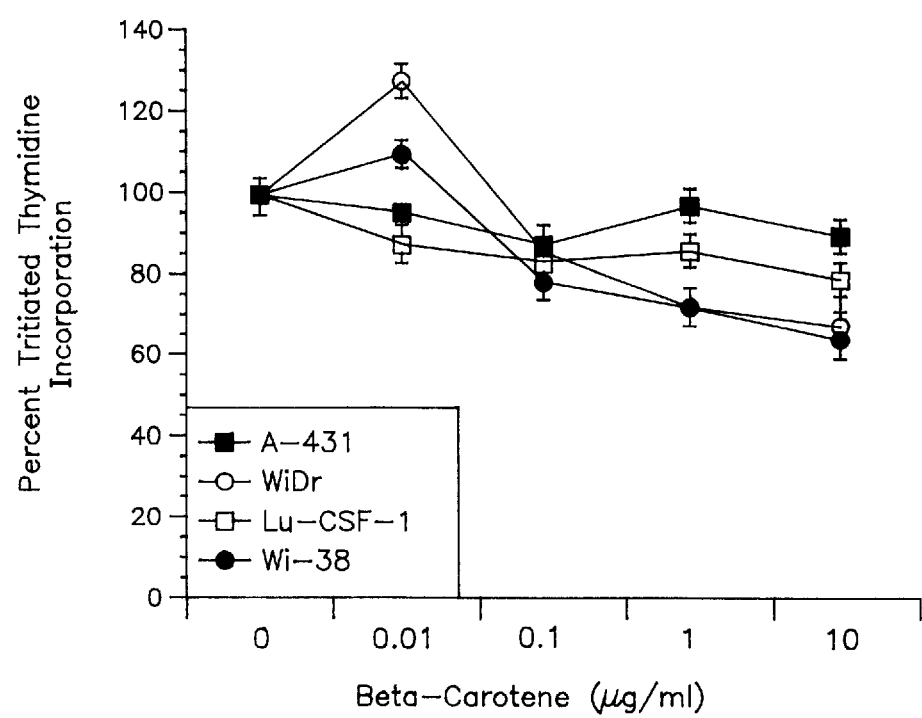

FIG. 4 is a graph showing the effect of beta-carotene on DNA synthesis in human tumor and normal cell lines. In summary, A431, epidermoid carcinoma; WiDr, colon adenocarcinoma; WI-38, fetal lung fibroblasts and Lu-CSF-1, lung adenocarcinoma were incubated for 72 hours with beta-carotene. Each data point is the mean of 6 wells ± percent standard error as compared to control. Diluent (soy) concentration=0.05%.

Figure 5:
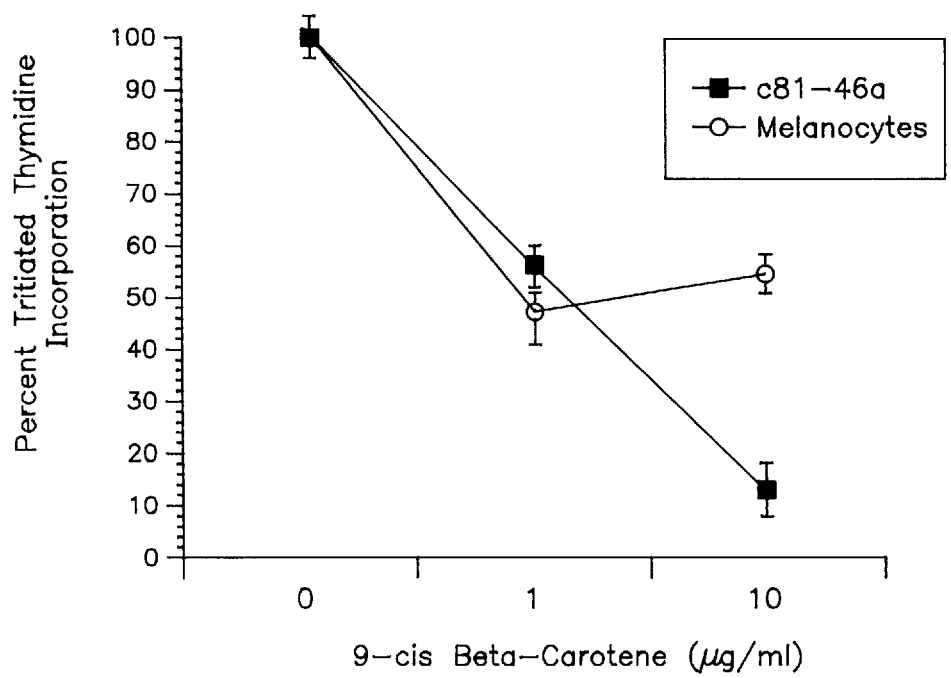

FIG. 5 is a graph showing the effect of 9-cis beta-carotene on DNA synthesis in human metastatic melanoma and neonatal melanocytes. In summary, the melanoma cell strain c81-46a and melanocytes were incubated for 72 hours with 9-cis beta-carotene. Each data point is the mean of 6 wells ± percent standard error as compared to control. Diluent (soy) concentration 0.05%.

FIGS. 1, 2 and 4 refer to "Percent Tritiated Thymidine Incorporation" which is a measure of DNA synthesis activity.

Details of the experiments conducted in relation to the invention are as follows.

Materials (a) Cell Cultures

In demonstrating the solubility and non-toxicity of the invention in experimentation concerning the treatment of melanomas and melanocytes it was necessary to first isolate and culture melanocytes and melanoma strains.

The method used to isolate and culture melanocytes is a combination of the procedures developed by Eisinger and Marko (see Eisinger M, Marko O: Selective proliferation of normal human melanocytes in vitro in the presence of phorbol ester and cholera toxin. Proc Natl Acad Sci 79:2018–2022, 1982) and Halaban and Alfano (see Halaban R., Alfano F.D.: Selective elimination of fibroblasts from cultures of normal human melanocytes. In Vitro 20:45–47, 1984).

Briefly, foreskin samples were collected from newborn infants, and the melanocytes isolated and transferred to a T-75 flask. Primary neonatal melanocytes were cultivated in MCDB 153 medium (Irvine Sci.) as described by Halaban (see Halaban R., Ghosh S., Baird A.: bFGF is the putative natural growth factor for normal human melanocytes. In Vitro Cell Develop Biol 23:47–52, 1987) and modified by Kath (see Kath R., Rodecsk U., Menssen H.D. et al: Tumor progression in the human melanocytic system: Anticancer Res 9:865–872, 1987). Fibroblast contamination was suppressed by adding geneticin (250 micrograms/ml) to the medium for 2 days. Melanoma cell strains (c81-46a, c81-46c, c81-61, c83-2c) were cultured in F-10 (Fisher Sci.) with 5% fetal calf serum, 5% newborn calf serum (Gemini Sci.), penicillin (100 units/ml) and streptomycin (0.1 milligrams/ml) (Sigma). The passage number for the melanoma cell strains used was less than 8, and the melanocytes was less than 5. The melanoma cell strains have previously been characterised (see Bregman M.D., Meyskens F.L.: Inhibition of human malignant melanoma colony-forming cells in vitro by prostaglandin Al, Canc Res 43:1642–1645, 1983; Thomson S.P., Meyskens F.L.: Methods of measurement of self-renewal capacity of clonogenic cells from biopsies of metastatic human malignant melanoma. Canc Res 42:4606–4613, 1982; and Yohem K.H., Slymen D.J., Bregman M.D., et al: Radiation survival of murine and human melanoma cells utilizing two assay systems; monolayer and soft agar. Br J Canc 57:64–69, 1987). A number of other tumour cell lines were also tested namely, A-431 (a human epidermoid carcinoma), WiDr (a human colon adenocarcinoma), Wl-38 (normal human fetal lung fibroblasts) (all obtained from the American Type Culture Collection) and Lu-CSF-1 (a human lung adenocarcinoma) (provided by the University of California at Irvine). These four cell lines were cultured in DMEM medium (Fisher Sci.), 5% fetal calf serum, 5% newborn calf serum, penicillin (100 units/ml) and streptomycin (0.1 milligrams/ml).

(b) Chemicals

The following chemicals were used in the testing of one form of the invention in the treatment of melanomas and melanocytes.

The beta-carotene was isolated from the alga Dunaliella salina and represented 85–90% of the total carotenoids, with half of the balance consisting of oxycarotenoids (lutein and zeaxanthin) and the remaining half of alpha-carotene. Gamma-carotene is normally undetectable as characterised by high pressure liquid chromatography. The soya bean oil was isolated from soya beans. A crystalline suspension of beta-carotene and soya bean oil was created. This resultant phase was then emulsified into the composition described. It was then sterilised by heat or filtration. Prior to testing on the cell lines each vial of the composition was sub-aliquoted into cryogenic vials (Costar) with a fresh vial used for each experiment. Throughout all procedures, beta-carotene was protected from direct light.

Tetrahydrofuran and ethanol (Fisher Sci.) of the highest quality available was used. Dimethylsulfoxide was purchased from Sigma.

The details of the emulsified beta-carotene composition are as follows:

|  |  | % by weight |
|---|---|---|
| (i) and (ii) | Beta-carotene | 2.4% |
|  | SOY being: |  |
|  | Soya bean oil | 6.8% |
|  | Glyceryl mono-oleate | 7.2% |
|  | Glycerol | 66.7% |
|  | Water | 16.9% |

The above composition can be prepared by the following method. A crystalline suspension of beta-carotene in soya bean oil is heated and glyceryl mono-oleate is added. This oil phase is dispersed in the glycerol-water phase by high shear mixing followed by homogenisation at 60°–70° C. Typically, a homogenisation pressure of 8,000 to 10,000 PSI is used, however, this pressure will vary according to the machine that is used. The resulting product is then sterilized heat processing. Typically, heat processing is effected by autoclaving at 121° C. for 15 minutes in a pack for dispensing (3 ml glass vial). Optionally, 0.3% of anti-oxidant tocopherols is added to overcome any toxicity that may develop over a period of time.

(c) Experimental Conditions

The following describes the experimental conditions that were used in the use of one form of the invention in the treatment of melanomas and melanocytes.

Incorporation of tritiated thymidine into DNA was measured in the following manner. Cells were seeded into a 96 well plate (Falcon) and allowed to grow to 50% confluency (24 hours) after which fresh medium alone, fresh medium with beta-carotene or fresh medium with a carrier (carrier concentration=0.05%) were added and incubated for 72 hours. DNA synthesis was measured by labelling with [methyl-3H]-thymidine (2.5 uCi/ml, 20 Ci/mmol Dupont-New England Nuclear) added to the medium during the last 15 hours of the treatment period. After incubation, cells were harvested using a PhD cell harvester (Cambridge Research Inc.). Radioactivity incorporated was determined by liquid scintillation counting (LS5000TD, Beckman Instruments) with an efficiency of 62.7%. The data is represented as percent tritiated thymidine incorporation as compared to control. Each data point is the mean of 6 wells ± percent standard error.

Cellular proliferation was determined as follows. Cells were seeded into 6 well plates (Falcon) and allowed to grow to 50% confluency (24 hours). Fresh medium and the appropriate compound was added and cells then incubated for 72 hours. After incubation, cells were harvested with 0.25% trypsin and washed. Cells were counted on a Coulter Counter (Coulter Instruments) and viability determined by trypan blue exclusion. Each data point is the mean of 3 wells ± percent standard error.

Results

FIG. 1 demonstrates the relative non-toxicity of the SOY carrier compared to the dose dependant toxic effect of tetrahydrofuran ("THF") and a 3:1 mixture of dimethylsulfoxide/ethanol ("DMSO/ETOH") on normal melanocytes and a metastatic melanoma strain c81-46, as measured by thymidine incorporation. THF, DMSO/ETOH and SOY were incubated with the cells for 72 hours at 0.005%, 0.05% and 0.5% concentration.

As shown in FIG. 1, the SOY did not effect incorporation of thymidine in the melanoma cells at any concentration of the diluent. THF had only a slight effect on the melanoma cells, while DMSO/ETOH decreased incorporation by 40% at the highest concentration.

FIG. 2 shows that the therapeutic agent, beta-carotene, in the SOY carrier was incorporated in normal melanocytes and four metastatic melanoma cell strains as demonstrated by the thymidine incorporation in these cells. At a concentration of 0.1 micrograms/ml, beta-carotene had a slight inhibitory effect on the melanoma cell growth. The most sensitive being c81-61 with a 20% decrease in DNA synthesis. However, the melanomas showed a differential response to beta-carotene at 1.0 micrograms/ml, ranging from no inhibition to greater than 40%. At the highest beta-carotene concentration (10 micrograms/ml), normal melanocytes and two of the melanomas (c81-61, c81-46c) were more than 95% inhibited.

Additionally, beta-carotene was effectively incorporated into the melanocyte and four metastatic melanoma cell strains as shown by the viability of these cells, as measured by trypan blue exclusion (FIG. 3). Beta-carotene at 1.0 micrograms/ml reduced viability by 20% while at 10 micrograms/ml no viable melanocytes were detected.

The response of other tumor types was also assessed for their response to beta-carotene (FIG. 4). The human epidermoid carcinoma cell line, A-431, was unaffected by beta-carotene even at 10 micrograms/ml. The colon cell line, the normal lung fibroblasts and the lung adenocarcinoma cell line were minimally inhibited (10–20%) demonstrating once again the incorporation of the beta-carotene.

FIG. 5 shows the effect of 9-cis beta carotene in the SOY carrier on normal melanocytes and one metastatic melanoma cell strain. At a concentration of 1.0 microgram/ml, both the normal melanocyte and the c81-46a were approximately 50% inhibited. At the higher concentration of 9-cis beta carotene (10.0 micrograms/ml), the metastatic melanoma cell strain was 90% inhibited while the melanocyte was slightly less inhibited than at 1.0 microgram/ml.

Without wishing to be limited to any specific theory, it appears that the mixture as illustrated in the examples is a superfine emulsion.

The useful properties of certain lipid based therapeutic agents have been in the past limited by the inability to introduce these agents into animals, including humans, by means of injection or intravenously. While these agents are capable of being substantially dissolved in certain solvents (for example, THF) they are not compatible with the blood or lymph of animals and are cytotoxic.

As a novel carrier for lipid based therapeutic agents, the SOY allows these therapeutic agents to be administered into animals and incorporated into the cells as substantially non-toxic water dispersible compositions. FIG. 1 demonstrates that the substantially non-toxicity of the SOY carrier and FIGS. 2 to 4 demonstrate that the substantially non-toxic water dispersible composition containing the substantially insoluble therapeutic agent has been incorporated into some of the cells as demonstrated by tritiated thymidine incorporation and trypan blue exclusion.

The claims defining the invention are as follows:

1. A therapeutic formulation for parenteral administration comprising:
   (a) a water soluble or dispersible component comprising glycerol in the range of 30 to 90% by weight;
   (b) an emulsifier in the range of 0.2% to 20% by weight; and
   (c) a water insoluble therapeutic formulation in a suitable carrier medium
       wherein the water insoluble therapeutic formulation is selected from the group
       consisting of carotenoid compositions and tocopherols.

2. A therapeutic formulation according to claim 1, wherein the emulsifier is selected from the group consisting of glycerides, polyglycerol esters, and phospholipids.

3. A therapeutic formulation according to claim 2, wherein the glyceride is glyceryl mono-oleate.

4. A therapeutic formulation according to claim 1, wherein the emulsifier is in the range of 1.0% to 10% by weight.

5. A therapeutic formulation according to claim 1, wherein the tocopherol is Vitamin E (D alpha tocopherol).

6. A therapeutic formulation according to claim 1, wherein the carotenoid composition comprises beta-carotene.

7. A therapeutic formulation according to claim 1, wherein the carotenoid composition comprises 2% to 50% by weight beta-carotene in soya bean oil composition.

8. A therapeutic formulation according claim 1, wherein the carotenoid composition comprises 20% to 40% by weight beta-carotene in a soya bean oil composition.

9. A therapeutic formulation according claim 1, wherein the carotenoid composition comprises 30% by weight beta-carotene in a soya bean oil composition.

10. A therapeutic formulation according to claim 6, wherein the beta-carotene is a mixture of cis beta-carotene and all trans beta-carotene.

11. A therapeutic formulation according to claim 10, wherein the cis beta-carotene content of the beta-carotene is in the range of 50% to 90%.

12. A therapeutic formulation according to claim 10, wherein the cis beta-carotene content of the beta-carotene is in the range of 70% to 85%.

13. A therapeutic formulation according to claim 10, wherein the cis beta-carotene is predominantly 9 cis beta-carotene.

14. A therapeutic formulation according to claim 10, wherein the cis beta-carotene is in the range of 60% to 90% 9 cis beta-carotene.

15. A therapeutic formulation according to claim 1, wherein the water insoluble therapeutic agent is in the range of 0.1% to 10% by weight of the formulation.

16. A therapeutic formulation according to claim 1, wherein the water insoluble therapeutic agent is in the range of 1% to 5% by weight of the formulation.

17. A therapeutic formulation according to claim 1, wherein the carrier medium used to carry the water insoluble therapeutic formulation is selected from the group consisting of fatty acids, triglyceride lipids, non-saponifiable lipid preparations, petroleum hydrocarbons, and combinations thereof.

18. A therapeutic formulation according to claim 17, wherein the carrier medium comprises one or more triglyceride lipids selected from the group consisting of plant fats, plant oils, animal fats, and animal oils.

19. A therapeutic formulation according to claim 1, wherein the carrier medium is in the range of 0.1% to 40% by weight.

20. A therapeutic formulation according to claim 1, wherein the carrier medium is in the range of 1% to 20% by weight.

21. A therapeutic formulation according to claim 1, wherein the formulation further comprises one or more diluents selected from the group consisting of aqueous buffers, normal intravenous preparations and blood serum.

22. A therapeutic formulation according to claim 17, wherein the carrier medium comprises the petroleum hydrocarbon octadecane.

23. A therapeutic formulation according to claim 18, wherein the carrier medium comprises one or more vegetable oils selected from the group consisting of soya bean, cotton seed and sunflower oils.

24. A therapeutic formulation according to claim 18, wherein the carrier medium comprises one or more animal oils or fats selected from the group consisting of fish oil and beef fat.

25. A therapeutic formulation for parenteral administration comprising:
   (a) a water soluble or dispersible component comprising glycerol in the range of 30 to 90% by weight;
   (b) an emulsifier in the range of 0.2% to 20% by weight; and
   (c) a water insoluble therapeutic formulation in a suitable carrier medium, wherein the water insoluble therapeutic formulation comprises an active ingredient selected from the group consisting of carotenoids and tocopherols.

* * * * *